(12) United States Patent
VanRheenen

(10) Patent No.: US 8,044,223 B2
(45) Date of Patent: Oct. 25, 2011

(54) CRYSTALLINE 19-NORSTEROIDS

(75) Inventor: Verlan H. VanRheenen, Kalamazoo, MI (US)

(73) Assignee: Bridge Organics Co., Vicksburg, MI (US)

( * ) Notice: Subject to any disclaimer, the term of this patent is extended or adjusted under 35 U.S.C. 154(b) by 1743 days.

(21) Appl. No.: 10/815,351

(22) Filed: Apr. 1, 2004

(65) Prior Publication Data

US 2005/0222109 A1   Oct. 6, 2005

Related U.S. Application Data

(60) Provisional application No. 60/460,486, filed on Apr. 4, 2003.

(51) Int. Cl.
*C07J 5/00* (2006.01)
(52) U.S. Cl. .................................................. 552/595
(58) Field of Classification Search .................. 552/595
See application file for complete search history.

(56) References Cited

U.S. PATENT DOCUMENTS

2002/0025951 A1 * 2/2002 Kim et al.

FOREIGN PATENT DOCUMENTS

WO   WO 01/47945 A1 * 7/2001

OTHER PUBLICATIONS

Berge et al., Pharmaceutical salts. Journal of Pharmaceutical Sciences, vol. 66(1), pp. 1-19, 1977.*

* cited by examiner

*Primary Examiner* — Barbara P Badio
(74) *Attorney, Agent, or Firm* — Price Heneveld LLP

(57) ABSTRACT

The present invention are two crystalline salts, 17α-acetoxy-21-methoxy-11β-(4-,N,N-dimethylaminophenyl)-19 norpregna-4,9-diene-3,20-dione hydrochloride and 17α-acetoxy-21-methoxy-11β-(4-,N,N-dimethylaminophenyl)-19 norpregna-4,9-diene-3,20-dione hydrobromide, of the corresponding free base which is an amorphous solid.

4 Claims, No Drawings

CRYSTALLINE 19-NORSTEROIDS

CROSS-REFERENCE TO RELATED APPLICATIONS

This patent application claims the benefit of U.S. provisional patent application Ser. No. 60/460,486, filed Apr. 4, 2003 under 35 U.S.C. §119(e)(i).

BACKGROUND OF THE INVENTION

1. Field of the Invention

The present invention produces crystalline salts of a known 19-norsteroid which are useful as antiprogestational agents.

2. Description of the Related Art

International Publication WO97/41145 of PCT/US97/07373 patent application discloses 11β-(4-substitued)phenyl-21-substituted-19-norprogesterone derivatives useful as antiprogestational agents and processes to prepare these compounds. More specifically, International Publication WO97/41145 discloses 17α-acetoxy-21-methoxy-11β-(4-,N,N-dimethylaminophenyl)-19-norpregna-4,9-diene-3,20-dione, see Example IX, Step 10, compound 38. The 11β-(4-substitued)phenyl-21-substituted-19-norprogesterone derivatives are amorphous solids and difficult to work with. The compounds of the present invention are crystalline solids which are much easier to work with for pharmaceutical compounding purposes.

International Publication WO01/74840 of PCT/US01/08681 patent application discloses additional 11β-(4-substitued)phenyl-21-substituted-19-norprotesterone derivatives with the same utility as set forth in International Publication WO97/41145.

SUMMARY OF INVENTION

Disclosed is 17α-acetoxy-21-methoxy-11β-(4-,N,N-dimethylaminophenyl)-19 norpregna-4,9-diene-3,20-dione hydrochloride.

Also disclosed is 17α-acetoxy-21-methoxy-11β-(4-,N,N-dimethylaminophenyl)-19 norpregna-4,9-diene-3,20-dione hydrobromide.

Further disclosed is that the above salts are in crystalline form.

DETAILED DESCRIPTION OF THE INVENTION

The biologically active 11β-substituted free amine (I, see Chart A), 17α-acetoxy-21-methoxy-11β-(4-,N,N-dimethylaminophenyl)-19-norpregna-4,9-diene-3,20-dione, is known, see International Publication WO97/41145, see Example IX, compound 38. This compound is a tertiary amine, —N(CH$_3$)$_2$ and as the free base, is an amorphorous solid that is difficult to isolate, characterize and establish the high purity required for an API (Active Pharmaceutical Ingredient). The 11β-substituted salts (II, see Chart A), in particular the hydrochloride and hydrobromide, are stable, crystalline solids that are readily characterized, and have properties suitable for an API. The hydrochloride and hydrobromide salts are prepared by dissolving the corresponding free base 11β-substituted free amine (I) in suitable organic solvent including but not limited to acetone, ethyl acetate, acetonitrile, ethanol, ether, MTBE, isopropinol and mixtures thereof. The preferred solvent mixture is made up of acetone, ethyl acetate and ether. To an approximate 1 molar solution of the 11β-substituted free amine (I) in a suitable solvent at about 20-25° is added one equivalent of hydrogen chloride or hydrogen bromide either as a gas or in solution. Suitable conditions, include using the 11β-substituted free amine (I) at a concentration of about 0.1 to about 10 molar, the temperature of about 20-25° C.±40°, and the solution of HCl or HBr which may be in water or in a suitable organic solvent as defined above. Preferred is a 1 molar solution of the 11β-substituted free amine (I) in a suitable solvent at 20-25° C. to which is added hydrogen chloride. The crystalline mass formed is cooled, filtered, washed with a small amount of cold solvent, and dried to constant weight under reduced pressure. This solid crystalline material may be recrystallized from a suitable solvent such as those set forth above. The preferred solvent system is ethanol/ether.

The 11β-substituted salts (II) have the same utility as do the 11β-substituted free amine (I) which is set forth in International Publication WO97/41145 and is as an antiprogestational agent.

Definitions and Conventions

The definitions and explanations below are for the terms as used throughout this entire document including both the specification and the claims.

Definitions

All temperatures are in degrees Celsius.

TLC refers to thin-layer chromatography.

NMR refers to nuclear (proton) magnetic resonance spectroscopy, chemical shifts are reported in ppm (d) downfield from TMS.

[a]$_D^{25}$ refers to the angle of rotation of plane polarized light (specific optical rotation) at 25° with the sodium D line (589 nm).

MTBE refers to methyl t-butyl ether.

Ether refers to diethyl ether.

Pharmaceutically acceptable refers to those properties and/or substances which are acceptable to the patient from a pharmacological/toxicological point of view and to the manufacturing pharmaceutical chemist from a physical/chemical point of view regarding composition, formulation, stability, patient acceptance and bioavailability.

When solvent pairs are used, the ratios of solvents used are volume/volume (v/v).

When the solubility of a solid in a solvent is used the ratio of the solid to the solvent is weight/volume (wt/v).

EXAMPLES

Without further elaboration, it is believed that one skilled in the art can, using the preceding description, practice the present invention to its fullest extent. The following detailed examples describe how to prepare the various compounds and/or perform the various processes of the invention and are to be construed as merely illustrative, and not limitations of the preceding disclosure in any way whatsoever. Those skilled in the art will promptly recognize appropriate variations from the procedures both as to reactants and as to reaction conditions and techniques.

Example 1

17α-Acetoxy-21-methoxy-11β-(4-,N,N-dimethylaminophenyl)-19-norpregna-4,9-diene-3,20-dione Hydrochloride (II)

Hydrogen chloride (1.1 M, 8.5 ml) in ether is added dropwise to 17α-acetoxy-21-methoxy-11β-(4-,N,N-dimethylaminophenyl)-19-norpregna-4,9-diene-3,20-dione (I, International Publication WO97/41145, Example IX, compound 38, 9.31 Mm) in acetone (9.4 ml) and ethyl acetate (48 ml). The reaction mixture is stirred vigorously. After stirring 2 hours at 20-25° followed by 2 hours below 0° C., the solid is filtered, washed with cold ethyl acetate and dried to constant weight. The product hydrochloride is recrystallized from ethanol/ethyl ether to give the title compound, mp=187-187.5° C.; $[\alpha]_D$ 1% $CHCl_3$ +48.5°; NMR ($CDCl_3$)=0.34, 2.12, 3.17, 3.43, 4.22, 4.49, 5.83, 7.30 and 7.70 δ.

Example 2

17α-Acetoxy-21-methoxy-11β-(4-,N,N-dimethylaminophenyl)-19-norpregna-4,9-diene-3,20-dione Hydrobromide (II)

Hydrogen bromide (30%, 0.16 ml) in acetic acid diluted with hexane and THF is added to 17α-acetoxy-21-methoxy-11β-(4-N,N-dimethylaminophenyl)-19-norpregna-4,9-diene-3,20-dione (I, 0.8 Mm). The resulting semi-solid is dissolved by adding ethanol, and the solvents removed under reduced pressure to give a concentrate. The concentrate is dissolved in acetone, ethyl acetate is added to the turbidity point, and crystallization occurs on standing at 20-25°. After standing two days at −15° C. the crystals are filtered, washed with cold acetone and dried at 50° to give the title compound, NMR($CDCl_3$)=0.33δ, 2.12, 3.18, 3.44, 4.23, 4.50, 5.84, 7.33 and 7.73 δ.

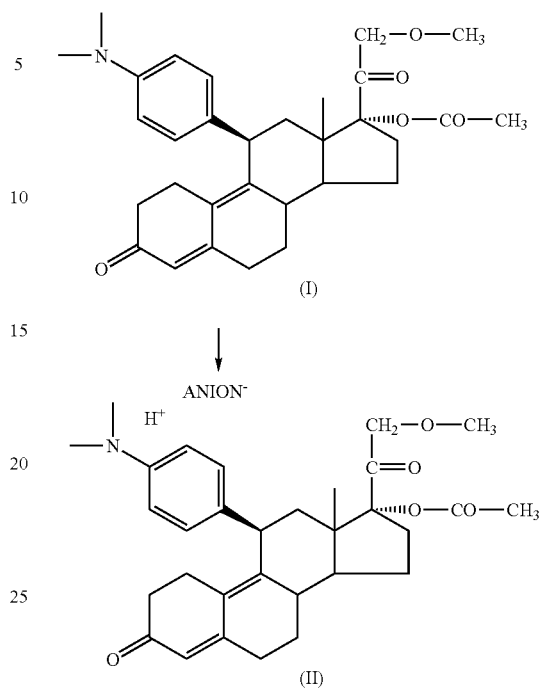

CHART A

The invention claimed is:
1. 17α-Acetoxy-21-methoxy-11β-(4-,N,N-dimethylaminophenyl)-19-norpregna-4,9-diene-3,20-dione hydrochloride.
2. A compound according to claim 1 which is 17α-acetoxy-21-methoxy-11β-(4-,N,N-dimethylaminophenyl)-19-norpregna-4,9-diene-3,20-dione hydrochloride in crystalline form.
3. 17α-Acetoxy-21-methoxy-11β-(4-,N,N-dimethylaminophenyl)-19-norpregna-4,9-diene-3,20-dione hydrobromide.
4. A compound according to claim 3 which is 17α-acetoxy-21-methoxy-11β-(4-,N,N-dimethylaminophenyl)-19-norpregna-4,9-diene-3,20-dione hydrobromide in crystalline form.

* * * * *